United States Patent
Fernandez

(10) Patent No.: US 7,998,126 B1
(45) Date of Patent: Aug. 16, 2011

(54) INTEGRAL URINE COLLECTOR

(76) Inventor: Benidecto Fernandez, Hialeah, FL (US)

( * ) Notice: Subject to any disclaimer, the term of this patent is extended or adjusted under 35 U.S.C. 154(b) by 1469 days.

(21) Appl. No.: 11/173,637

(22) Filed: Jul. 5, 2005

Related U.S. Application Data

(63) Continuation-in-part of application No. 10/287,885, filed on Nov. 6, 2002, now abandoned.

(51) Int. Cl.
*A61F 5/44* (2006.01)
(52) U.S. Cl. .......................... 604/329; 604/319; 604/326
(58) Field of Classification Search .................. 604/319, 604/322, 326, 327, 329, 544
See application file for complete search history.

(56) References Cited

U.S. PATENT DOCUMENTS 4,492,258 A * 1/1985 Lichtenstein et al. ............ 141/1
4,681,573 A * 7/1987 McGovern et al. ........... 604/329

OTHER PUBLICATIONS

U.S. Appl. No. 10/287,885, filed Nov. 6, 2002, Benidecto Fernandez.

* cited by examiner

*Primary Examiner* — Lynne Anderson
(74) *Attorney, Agent, or Firm* — Sanchelima & Associates, P.A.

(57) ABSTRACT

A urine collector for females that use a frustropyramidal funnel member with a narrow end that has a rhombus-shape cross-section that a user can deform to fit a cooperating locking assembly with a frustropyramidal through aperture. As the deforming pressure on the folds of the funnel member is released, the outer walls of the narrow end of the funnel engage the internal walls of a frustropyramidal central through aperture in the locking assembly keeping the funnel member in place. The locking assembly can be integrally built in the collecting container or in a separate closure locking assembly.

6 Claims, 4 Drawing Sheets

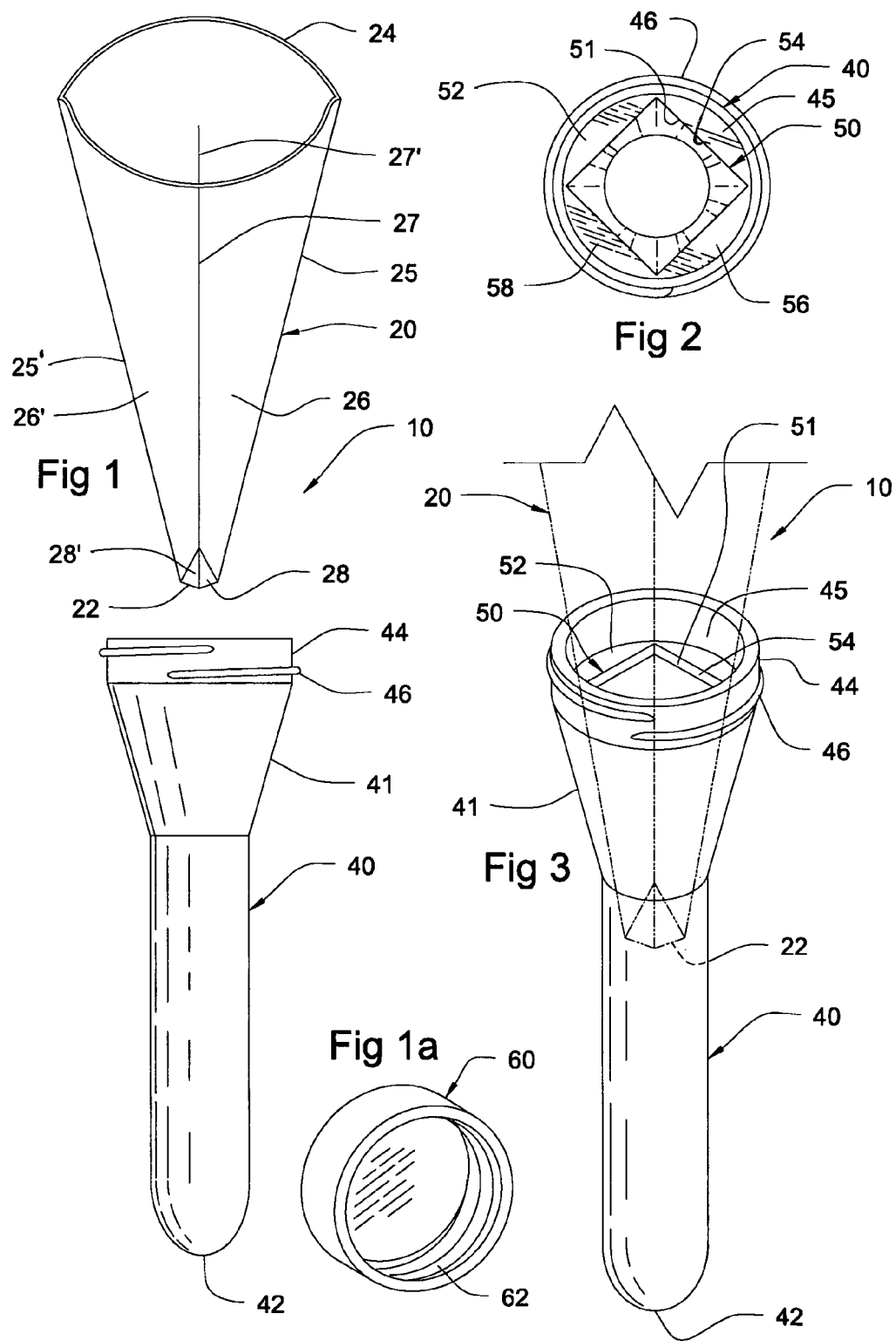

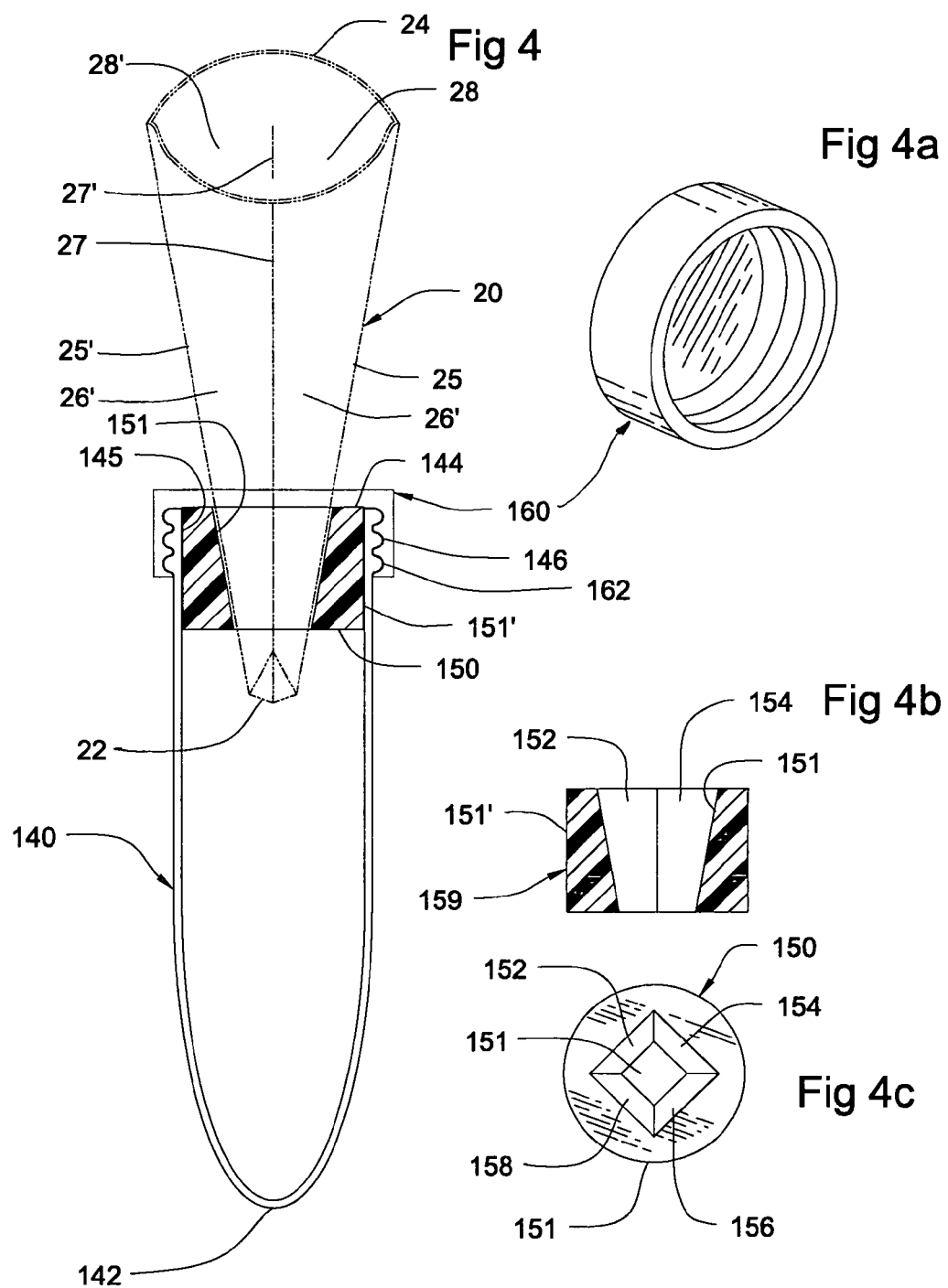

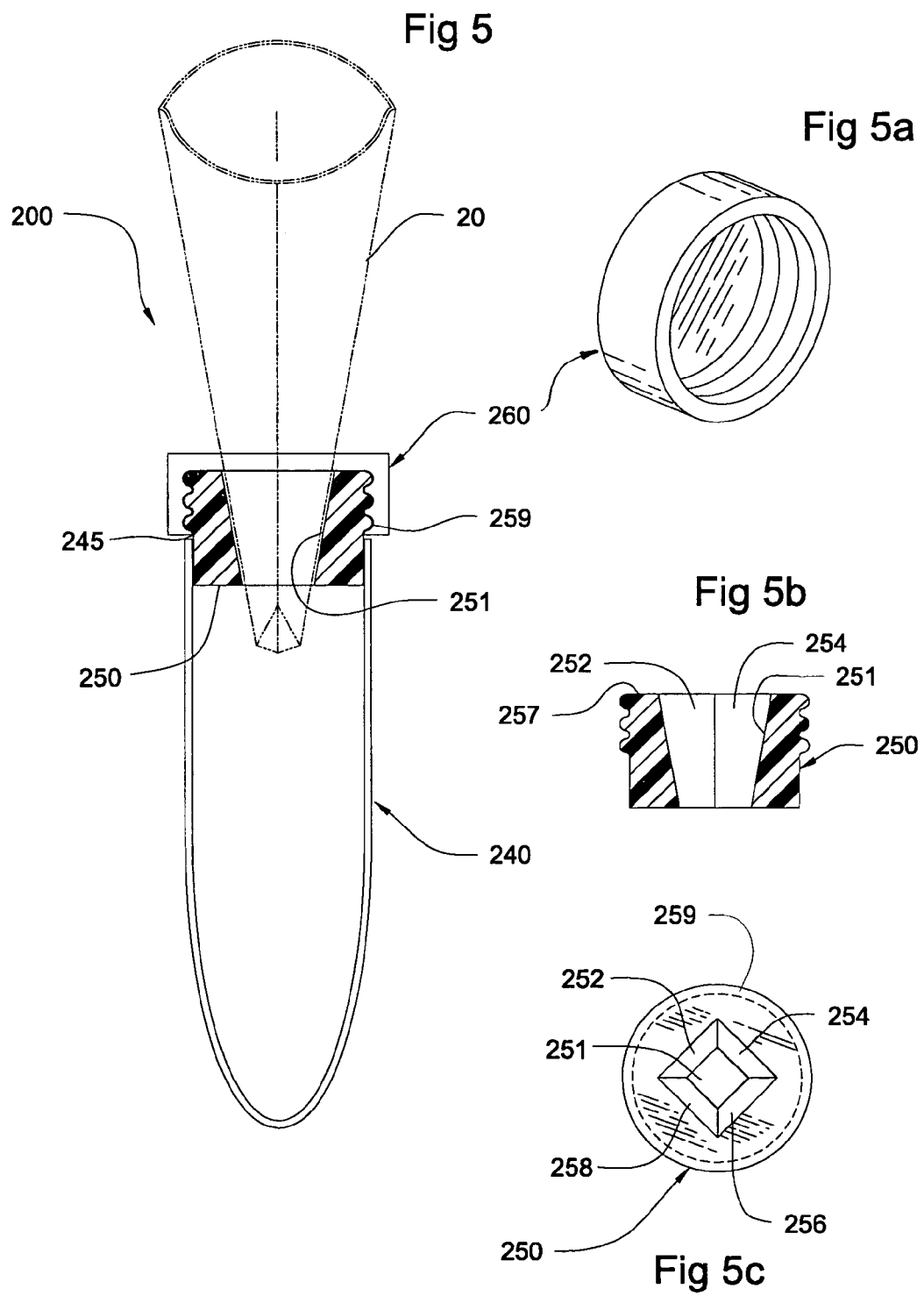

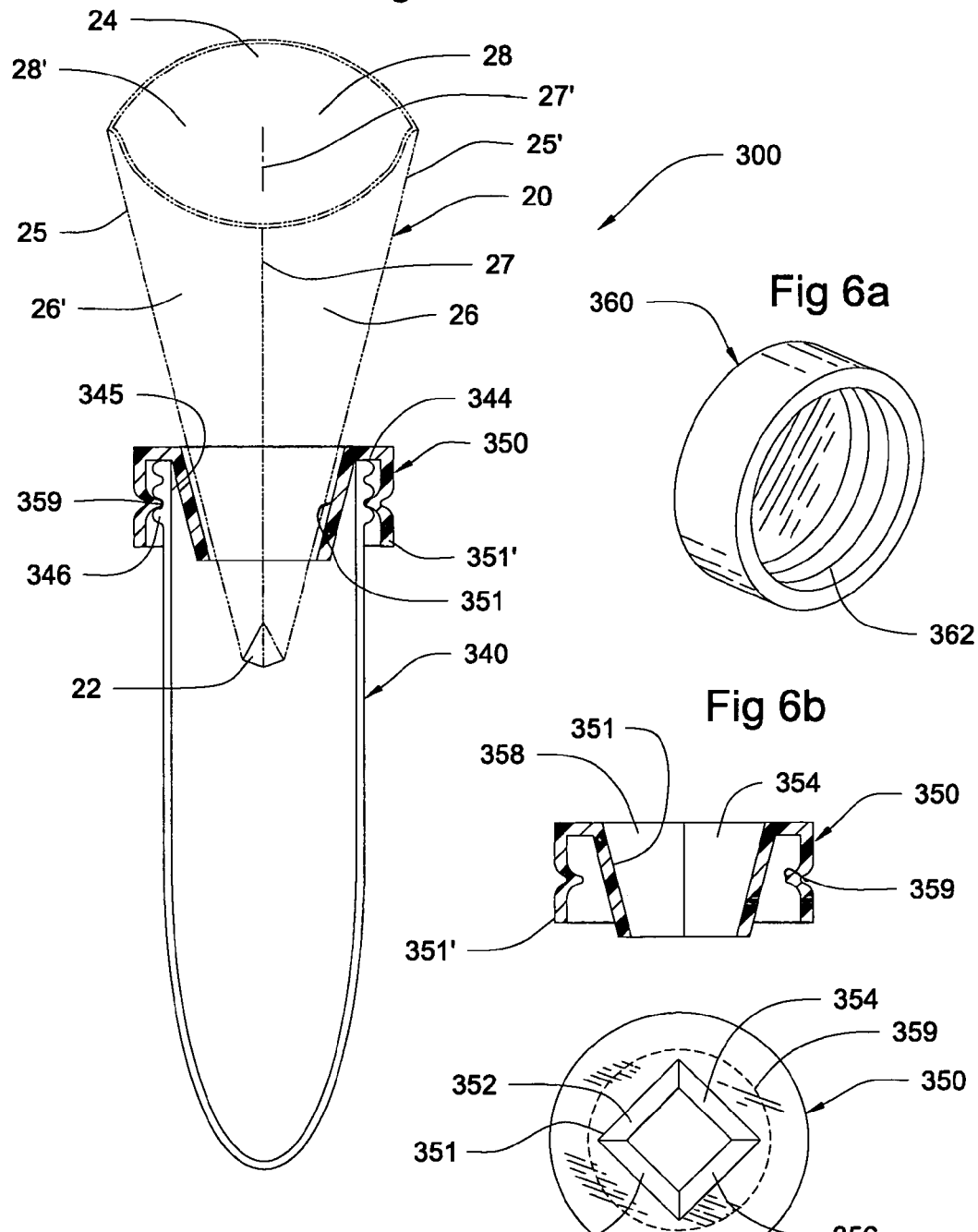

INTEGRAL URINE COLLECTOR

OTHER RELATED APPLICATIONS

The present application is a continuation-in-part of of U.S. patent application Ser. No. 10/287,885, filed on Nov. 6, 2002, now abandoned which is hereby incorporated by reference.

BACKGROUND OF THE INVENTION

1. Field of the Invention

The present invention relates to an integral urine collector.

2. Description of the Related Art

Several designs for urine collectors have been designed in the past. None of them, however, includes a frustoconical member integrally mounted to the open end of the collection tube to facilitate the insertion of a removable funnel member and the collection of the urine without spillage.

Applicant believes that the closest reference corresponds to his pending U.S. patent application Ser. No. 10/287,885, filed on Nov. 6, 2002, for a urine collector. However, it differs from the present invention because the present application has a frustoconical member integrally built in a collection tube adjacent to the open end. The frustoconical member includes an internal locking block with a rhombus-shape internal through aperture that cooperatively receives the narrow end of the removable funnel member to facilitate the collection of the urine. The funnel member typically has a flat configuration when at rest, which a user can readily resiliently deform by pressing on the longitudinal edges or folds. The cross-section of the narrow end changes from a flattened rhombus shape to a square shape and, if the force applied increases, it acquires a rhombus shape again. To match the cross-section of the internal through aperture, in the preferred embodiment a user depresses the narrow end until a square cross-section is achieved and the narrow end is inserted therethrough until the frustropyramidal shape causes the walls to engage those of the funnel locking assembly. None of the urine collectors provide for such a mechanism that avoids drastic movements that are susceptible to cause spillages. Many old and handicapped patients have difficulties with the prior art mechanisms.

Other patents describing the closest subject matter provide for a number of more or less complicated features that fail to solve the problem in an efficient and economical way. None of these patents suggests the novel features of the present invention.

SUMMARY OF THE INVENTION

It is one of the main objects of the present invention to provide an easy to manipulate urine collector device that avoids spillage and contamination of the urine sample.

It is another object of this invention to provide a urine collector that utilizes a minimum number of parts and that can be readily assembled and disassembled without requiring specialized handling.

It is still another object of the present invention to provide a urine collector that permits a female user to void and collect her urine sample while standing up.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description; when read in conjunction with the accompanying drawings in which:

FIG. 1 represents a front elevational view of one of the preferred embodiments for the urine collector subject of the present application.

FIG. 1*a* is an isometric view of the cap for the urine collector shown in FIG. 1.

FIG. 2 shows a top view of the container used with the collector system shown in FIG. 1.

FIG. 3 illustrates an isometric view of the container shown in the previous figures showing the internal built-in locking block with its internal through aperture engaging a funnel member shown in phantom.

FIG. 4 represents a front elevational view of another preferred embodiment for the urine collector subject of the present application wherein the funnel locking assembly is snuggly received inside the container. The locking assembly is cross-sectioned to show the central frustropyramidal through opening. The funnel member is shown in phantom.

FIG. 4*a* is an isometric view of the cap for the urine collector shown in FIG. 4.

FIG. 4*b* shows a front elevational cross-section view of the funnel locking assembly used with the embodiment represented in FIG. 4.

FIG. 4*c* shows a top view of the funnel locking assembly used with the embodiment for collector system shown in FIG. 4.

FIG. 5 represents a front elevational view of another alternate embodiment for the urine collector subject of the present application wherein the funnel locking assembly is partially and snuggly received inside the container and the portion outside the container includes an external thread that mates with the internal thread of the cap member. The locking assembly is cross-sectioned to show the central frustropyramidal through opening. The funnel member is shown in phantom.

FIG. 5*a* is an isometric view of the cap for the urine collector shown in FIG. 5.

FIG. 5*b* shows a front elevational cross-section view of the funnel locking assembly used with the embodiment represented in FIG. 5.

FIG. 5*c* shows a top view of the funnel locking assembly used with the embodiment for collector system shown in FIG. 5.

FIG. 6 represents a front elevational view of another alternate embodiment for the urine collector subject of the present application wherein a container or test tube with an external thread at the upper end is used and the funnel locking assembly is releasably mounted to the container's external threads. The locking assembly is cross-sectioned to show the central frustropyramidal through opening. The funnel member is shown in phantom.

FIG. 6*a* is an isometric view of the cap for the urine collector shown in FIG. 6.

FIG. 6*b* shows a front elevational cross-section view of the funnel locking assembly used with the embodiment represented in FIG. 6.

FIG. 6c shows a top view of the funnel locking assembly used with the embodiment for collector system shown in FIG. 6.

DETAILED DESCRIPTION OF THE PREFERRED EMBODIMENT

Referring now to the drawings, where the present invention is generally referred to with numeral 10, it can be observed that it basically includes resilient frustropyramidal funnel member 20, container 40 and cap 60, as seen in FIGS. 1 and 1a.

As seen in FIG. 1, resilient frustropyramidal funnel member 20 has ends 22 and 24 and longitudinally extending opposite folds 25 and 25' and 27 and 27' defining front walls 26 and 26' and rear walls 28 and 28'. Resilient frustropyramidal funnel member 20 is narrower at end 22 and broadens towards end 24. At rest, funnel member 20 has a flattened rhombus-shape cross-section that is resiliently deformable.

As seen in FIGS. 2 and 3, container 40 has ends 42 and 44. End 42 is closed and end 44 has opening 45 with external threaded portion 46. Container 40 also includes locking assembly 50 interiorly mounted adjacent to opening 45.

Locking assembly 50 includes central through aperture 51 defined by the separation of internal walls 52; 54; 56 and 58, as best seen in FIG. 2. Aperture 51 has a substantially square shape and cooperates to receive narrower end 22 of funnel member 20 passing a predetermined distance through locking assembly 50. Portion 41 is adjacent to end 44. Portion 41 has a frustoconical shape and houses locking assembly 50 therein. A user deforms narrower end 22 of funnel member 20 by pressing on folds 25 and 25' thereby causing the cross-section of member 20 to go from a flattened rhombus shape to a substantially square shape that mates with aperture 51. After narrower end 22 is inserted and passes through locking assembly 50, a user releases folds 25 and 25' permitting resilient funnel member 20 to urge its cross section towards the at rest rhombus shape. Internal walls 52; 54; 56 and 58 lockingly coact with walls 26; 26'; 28 and 28', as best seen in FIG. 3.

Cap 60 is removably and selectively mounted to end 44 of container 40. As shown in FIG. 1a, cap 60 has internal threads 62 that cooperatively mate with external threaded portion 46 to removably mount cap 60 to end 44.

To deposit the urine sample, a user unscrews cap 60 to open end 44 of sterilized container 40. Then, she inserts narrower end 22 of resilient frustropyramidal funnel member 20 through opening 45 and locking assembly 50, as shown in FIG. 3. The user conveniently places resilient frustropyramidal funnel member 20 next to her body and collects a predetermined amount of urine by filling container 40. Once completed the urine collection process, the user removes funnel member 20 by applying pressure to folds 25 and 27. Finally, the user closes container 40 with cap 60.

Alternate embodiments are shown in FIGS. 4 through 6b. The first alternate embodiment 100 is shown in FIGS. 4; 4a; 4b and 4c. Funnel locking assembly 150 has, in this alternate embodiment, a substantially cylindrical shape with internal frustropyramidal through aperture 151 having a smaller diameter than external cylindrical portion 151'. Locking assembly 150 is a removable closure in this embodiment. Internal frustropyramidal through aperture 151 includes internal walls 152; 154; 156 and 158 that frictionally coact with walls 26; 26'; 28 and 28' of funnel member 20 to lock in the latter in place. External cylindrical wall 151' has cooperative dimensions to fit opening 145 of collecting container 140, which is preferably a conventional inexpensive container or a test tube. Container 140 also includes closed end 142 and external thread 146 next to upper end 144 for removably receiving cap member 160.

As in the other embodiment 200 represented in FIGS. 5; 5a; 5b and 5c, funnel locking closure assembly 250 includes internal frustropyramidal through aperture 251 with internal walls 252; 254; 256 and 258 that define a rhombus cross-section, as best seen in FIG. 5c. Locking closure assembly 250 has a substantially cylindrical or slight frustoconical shape and it is partially and snugly received through opening 245 of collecting container 240. Locking closure assembly 250 to include external thread 259 next to upper end 257 for removably receiving cap member 260. Walls 252; 254; 256 and 258 frictionally coact with walls 26; 26'; 28 and 28' of funnel member 20 to lock the latter in place.

Another alternate embodiment is designated with numeral 300 and is shown in FIGS. 6, 6a, 6b and 6c. Funnel locking closure assembly 350 includes, in this alternate embodiment, internal frustropyramidal tubular member 351 with a tapered rhombus cross-section and a central pyramidal through aperture that abuttingly co-act with walls 26; 26'; 28 and 28' locking funnel member 20 in place. Funnel locking closure assembly 350 also includes external resilient peripheral skirt 351'. External peripheral skirt 351' includes internal annular rib 359 that removably and cammingly engage to peripheral grooves or threads 346 of container 340. Internal frustropyramidal tubular member 351 includes internal walls 352; 354; 356 and 358, as best seen in FIG. 6c, to frictionally coact with walls 26; 26'; 28 and 28' of funnel member 20 to lock the latter in place. The upper end of internal frustropyramidal tubular member 351 includes a top wall perpendicular extending from peripheral skirt 351', that has cooperative dimensions to fit opening 345 of collecting container 340, which is preferably a conventional inexpensive container or a test tube with external thread 346 next to upper end 344 for removably receiving its cap 360, shown in FIG. 6a. Internal threads 362 of cap 360 cooperatively mate with external threads 346 of end 344.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A urine collector for females, comprising:
   A) a resilient frustropyramidal funnel member having first and second ends with first and second longitudinally extending opposite folds defining front and rear walls being narrower at said first end and broadening towards said second end, and said funnel member having an at rest rhombus-shape cross-section that is resiliently deformable; and
   B) a container having third and fourth ends, said third end being closed and said fourth end having an opening, and said container further including a locking assembly interiorly mounted adjacent to said opening and said locking assembly having a central through aperture having internal walls that define a rhombus cross-section that cooperate to receive said first end a predetermined distance inside said through aperture and rear and front walls coact with said internal walls to releasably lock said funnel member in place so that drastic movements are avoided.

2. The urine collector set forth in claim 1 further including:
   C) cap means removably and selectively mounted to said fourth end.

3. The urine collector set forth in claim 2 wherein said fourth end includes a frustoconical-shaped portion to increase said central through aperture and the area where said front and rear walls abut said internal walls.

4. A urine collector for females, comprising:
   A) a resilient frustropyramidal funnel member having first and second ends with first and second longitudinally extending opposite folds defining front and rear walls being narrower at said first end and broadening towards said second end, and said funnel member having an at rest rhombus-shape cross-section that is resilient deformable;
   B) a container having third and fourth ends, said third end being closed and said fourth end having an opening;
   C) funnel locking closure means having cooperative dimensions to be snuggly at least partially received inside said container through said opening, and said funnel locking closure means including an internal frustropyramidal through aperture with a substantially rhombus cross-section and said through aperture being defined by internal walls that abuttingly coact with said front and rear walls locking said funnel member in place so that drastic movements are avoided; and
   D) cap means removably and selectively mounted to said fourth end.

5. The urine collector set forth in claim 4, wherein said funnel locking means includes first and second portions being removably received within said container and said second portion protruding outside said container when said first portion is received therein, and said second portion further including external thread means, and said cap means including internal thread means for cooperatively mating with said second external thread means.

6. A urine collector for females, comprising:
   A) a resilient frustropyramidal funnel member having first and second ends with first and second longitudinally extending opposite folds defining front and rear walls being narrower at said first end and broadening towards said second end, and said funnel member having an at rest rhombus-shape cross-section that is resilient deformable;
   B) a container having third and fourth ends, said third end being closed and said fourth end having an opening and at least one peripheral groove;
   C) funnel locking closure means having an external peripheral skirt with, an internal annular rib for removably and cammingly engaging said at least one peripheral groove, and said closure means further include a top wall perpendicularly extending from said skirt and a frustropyramidal tubular member with a tapered rhombus cross-section having a central pyramidal through aperture that abuttingly co-act with said front and rear walls locking said funnel member in place so that drastic movements are avoided; and
   D) cap means removably and selectively mounted to said fourth end.

* * * * *